United States Patent
Virr et al.

(10) Patent No.: US 11,806,472 B2
(45) Date of Patent: *Nov. 7, 2023

(54) CPAP SYSTEMS

(71) Applicant: ResMed Pty Ltd, Bella Vista (AU)

(72) Inventors: Alexander Virr, Balmain (AU); Cem Tarakci, Sydney (AU); John David Oates, Castle Hill (AU); Barton John Kenyon, Sydney (AU); Graham Stephen Cutcliffe, Sydney (AU); Nathan John Row, Sydney (AU)

(73) Assignee: ResMed Pty Ltd

( * ) Notice: Subject to any disclaimer, the term of this patent is extended or adjusted under 35 U.S.C. 154(b) by 83 days.

This patent is subject to a terminal disclaimer.

(21) Appl. No.: 17/667,179

(22) Filed: Feb. 8, 2022

(65) Prior Publication Data

US 2022/0160978 A1 May 26, 2022

Related U.S. Application Data

(63) Continuation of application No. 15/720,952, filed on Sep. 29, 2017, now Pat. No. 11,285,279, which is a
(Continued)

(30) Foreign Application Priority Data

Nov. 3, 2009 (AU) ............................... 2009905363
Dec. 7, 2009 (AU) ............................... 2009905945

(51) Int. Cl.
*A61M 16/00* (2006.01)
*A61M 16/08* (2006.01)
(Continued)

(52) U.S. Cl.
CPC .... *A61M 16/0051* (2013.01); *A61M 16/0069* (2014.02); *A61M 16/026* (2017.08);
(Continued)

(58) Field of Classification Search
CPC .......... A61M 16/0057; A61M 16/0063; A61M 16/0066; A61M 16/0069
See application file for complete search history.

(56) References Cited

U.S. PATENT DOCUMENTS

| 4,944,310 A | 7/1990 | Sullivan |
| 5,258,696 A | 11/1993 | Le |

(Continued)

FOREIGN PATENT DOCUMENTS

| EP | 1262208 A2 | 12/2002 |
| EP | 2039386 A1 | 3/2009 |

(Continued)

OTHER PUBLICATIONS

EP Search Report dated Mar. 30, 2021 for EP Application No. 20196235.4.

(Continued)

*Primary Examiner* — LaToya M Louis
(74) *Attorney, Agent, or Firm* — Botos Churchill IP Law LLP

(57) ABSTRACT

A CPAP system includes a flow generator (10), a patient interface (50), an air delivery conduit (20) that interconnects the flow generator and the patient interface, wherein the air delivery conduit has an internal diameter of less than 19 mm. Preferably the air delivery conduit has an internal diameter of between about 10 mm and about 18 mm. The CPAP system may also include a controller for compensating for pressure swings and/or increased impedance within the system. Preferably the blower includes a low inertia blower.

20 Claims, 5 Drawing Sheets

Related U.S. Application Data continuation of application No. 13/505,564, filed as application No. PCT/AU2010/001462 on Nov. 3, 2010, now Pat. No. 9,802,015.

(51) Int. Cl.
 *A61M 16/10* (2006.01)
 *A61M 16/16* (2006.01)

(52) U.S. Cl.
 CPC .... *A61M 16/0875* (2013.01); *A61M 16/1075* (2013.01); *A61M 16/1095* (2014.02); *A61M 16/16* (2013.01); *A61M 2016/0021* (2013.01); *A61M 2016/0027* (2013.01); *A61M 2016/0039* (2013.01); *A61M 2205/3365* (2013.01); *A61M 2205/3368* (2013.01); *A61M 2205/3653* (2013.01)

(56) References Cited

U.S. PATENT DOCUMENTS

| | | | |
|---|---|---|---|
| 5,704,345 | A | 1/1998 | Berthon-Jones |
| 5,865,173 | A | 2/1999 | Froehlich |
| 5,880,569 | A | 3/1999 | Suzuki et al. |
| 6,078,730 | A | 6/2000 | Huddart et al. |
| 6,203,502 | B1 | 3/2001 | Hilgendorf et al. |
| 6,219,490 | B1 | 4/2001 | Gibertoni et al. |
| 6,332,463 | B1 | 12/2001 | Farrugia et al. |
| 6,484,719 | B1 | 11/2002 | Berthon-Jones |
| 6,557,553 | B1 | 5/2003 | Borrello |
| 6,837,242 | B2 | 1/2005 | Younes |
| 2001/0004894 | A1 | 6/2001 | Bourdon |
| 2003/0172930 | A1 | 9/2003 | Kullik et al. |
| 2004/0118403 | A1 | 6/2004 | O'Connor et al. |
| 2005/0150505 | A1 | 7/2005 | Burrow et al. |
| 2005/0241640 | A1 | 11/2005 | Baecke et al. |
| 2006/0174885 | A1 | 8/2006 | Aylsworth et al. |
| 2007/0144519 | A1 | 6/2007 | Henry et al. |
| 2008/0009236 | A1 | 1/2008 | Dreher |
| 2008/0028850 | A1 | 2/2008 | Payton et al. |
| 2008/0105257 | A1 | 5/2008 | Paul et al. |
| 2008/0173305 | A1 | 7/2008 | Frater |
| 2008/0251076 | A1 | 10/2008 | Goeldi |
| 2009/0078259 | A1 | 3/2009 | Kooij et al. |
| 2010/0116272 | A1 | 5/2010 | Row et al. |
| 2010/0319697 | A1 | 12/2010 | Farrugia et al. |
| 2011/0088693 | A1 | 4/2011 | Somervell et al. |

FOREIGN PATENT DOCUMENTS

| | | | |
|---|---|---|---|
| GB | 2294400 | A | 5/1996 |
| WO | 9604043 | A1 | 2/1996 |
| WO | 9710868 | A1 | 3/1997 |
| WO | 2006019323 | A1 | 2/2006 |
| WO | 2006092001 | A1 | 9/2006 |
| WO | 2007019624 | A1 | 2/2007 |
| WO | 2007048206 | A1 | 5/2007 |
| WO | 2007134405 | A1 | 11/2007 |
| WO | 2009146484 | A1 | 12/2009 |
| WO | 2010081223 | A1 | 7/2010 |

OTHER PUBLICATIONS

"A Pattern to Evaluate Airway Resistive Phenomenon Using Rohrer's Equation", Advan in Physiol Edu 31:121, 2007.

"EP Search Report for Application No. EP10827711 dated Apr. 28, 2015".

"Extended EP Search Report for Application No. 10827711.2 dated Aug. 18, 2015".

"International Search Report to PCT/AU2010/001462 dated Jan. 31, 2011".

CPAP SYSTEMS

CROSS-REFERENCE TO RELATED APPLICATIONS

This application is a continuation of U.S. application Ser. No. 15/720,952, filed on Sep. 29, 2017, which is a continuation of U.S. application Ser. No. 13/505,564, filed on Jul. 25, 2012, now U.S. Pat. No. 9,802,015, which is a national phase entry under 35 U.S.C. § 371 of International Application No. PCT/AU2010/001462 filed Nov. 3, 2010, published in English, which claims priority from Australian Provisional Application No. 2009905945 filed Dec. 7, 2009, Australian Provisional Application No. 2009905363 filed Nov. 3, 2009, all of which are incorporated herein by reference.

FIELD OF THE INVENTION

The present invention relates to a PAP system and air delivery tubing that delivers breathable gas to a patient.

BACKGROUND OF THE INVENTION

Colin Sullivan was the first to invent the use of nasal Continuous Positive Airway Pressure (CPAP) to treat Obstructive Sleep Apnea (OSA), e.g., see U.S. Pat. No. 4,944,310. The treatment generally provides a supply of air or breathable gas from a blower to a patient via an air delivery conduit and a patient interface, such as a full-face or nasal mask or nasal prongs. The air or breathable gas is commonly delivered at a pressure of 3 $cmH_2O$ to 25 $cmH_2O$ and acts as a splint to hold the airway open during sleep.

Patient compliance and acceptance of CPAP therapy is a major driver of the industry. To address this issue, emphasis has been placed on reducing the size of CPAP systems to enhance the look and feel of the systems for patients. There are three major components in a CPAP system, i.e., a flow generator, an air delivery conduit, and a patient interface. To date, there has been a focus on reducing the size of the flow generator and developing less intrusive patient interfaces. However, there has been very little attention paid to the size of the air delivery conduit, which acts as the interface between the patient interface and the flow generator. For example, there is a Kaerys KXS CPAP machine that is supplied with 15 mm tubing. However, the tubing may only be used for pressures up to 15 $cmH_2O$. In order to effectively increase compliance, all components of a CPAP system should be reduced in size and allow a broad range of pressures to be delivered. A smaller CPAP system also provides for smaller packaging requirements.

The air delivery conduit typically used in CPAP therapy has been medical grade tubing as found in hospitals with an outer diameter of 22 mm and internal diameter of 19 mm. As CPAP therapy is generally conducted in the home, this medical tubing can make users apprehensive in adopting the therapy because the medical tubing can look out of place amongst the environment commonly found in a user's bedroom. In addition, the tubing may be bulky and not easily packed up or organized to preserve the look of a bedroom. Furthermore, the sound caused by the medical tubing as it brushes against linen and the added physical interference as far as drag to the patient interface can cause the user some discomfort. There is no current standard ISO tubing size other than 22 mm outer diameter available for use with CPAP systems across the full flow generator pressure range.

Also, current tubing can communicate airflow but are restrictive in communicating electrical signals. Currently, only external insulation, e.g., in the form of a sock or sheath over the tubing, has been added as an accessory to the tubing to reduce "rain out", which is the collection of water caused from the humidifier within the tubing.

The problems with using tubing with a smaller bore include the high impedance in the tube to provide the desired pressure at the patient interface. Presently, some flow generators are not able to supply sufficient power for the full pressure range required. Also, there are large pressure swings due to the flow generator not being able to respond quickly enough to changes in pressure. Thus, a need has emerged in the art to address these problems.

SUMMARY OF THE INVENTION

One aspect of the invention relates to an air delivery conduit for a CPAP system that is smaller in size and provides an easy and quick connection between the patient interface and flow generator. This arrangement will allow the entire CPAP system to be smaller and packaged more compactly.

Another aspect of the invention relates to a CPAP system that provides a more comfortable look and feel for the patient.

Another aspect of the invention relates to a CPAP system that provides less heat loss in the air delivery conduit. The air delivery conduit having a reduced overall surface area compared to a standard 22 mm outer diameter air delivery conduit.

Another aspect of the invention relates to a CPAP system comprising a heated air delivery conduit that requires less power consumption.

Another aspect of the invention relates to a CPAP system comprising a heated air delivery conduit that provides less rain out to improve patient comfort.

Another aspect of the invention relates to a CPAP system including a flow generator including a blower that supplies breathable gas at pressure, a patient interface, and an air delivery conduit interconnecting the flow generator and the patient interface. The air delivery conduit includes a conduit portion having an outer diameter less than 22 mm.

Another aspect of the invention relates to a CPAP system including a flow generator including a blower that supplies breathable gas at pressure, a patient interface, and an air delivery conduit interconnecting the flow generator and the patient interface. The air delivery conduit includes a conduit portion having an internal diameter less than 19 mm.

Yet another aspect of the invention relates to the use of a CPAP system including a flow generator including a low inertia blower that supplies breathable gas at pressure, a patient interface, an air delivery conduit interconnecting the flow generator and the patient interface, and a controller adapted to control the pressure delivered to the patient interface device, wherein the air delivery conduit has an internal diameter of less than 19 mm and the controller includes a feedforward control to compensate for pressure disturbances within the system.

Optionally, the blower supplies the breathable gas at a pressure of 3-25 $cmH_2O$ or at least 3-20 $cmH_2O$ (e.g., a full range of therapy pressures appropriate for CPAP).

Yet another aspect of the invention relates to a CPAP system including a flow generator providing an outlet, an air delivery conduit, a flow generator connector that couples one end of the air delivery conduit to the outlet of the flow generator, and a recognition system structured to recognize or identify a type of air delivery conduit that is connected to the CPAP system.

Further aspects of the invention are set out in the claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

A CPAP system generally includes a flow generator, an air delivery conduit, and a patient interface. In use, the flow generator generates a supply of pressurized air that is delivered to the patient via an air delivery conduit that includes one end coupled to the outlet of the flow generator and an opposite end coupled to the patient interface. The patient interface comfortably engages the patient's face and provides a seal. The patient interface may have any suitable configuration as is known in the art, e.g., full-face mask, nasal mask, oro-nasal mask, mouth mask, nasal prongs, etc. Also, any suitable headgear arrangement may be utilized to comfortably support the patient interface in a desired position on the patient's face.

Figure 1:
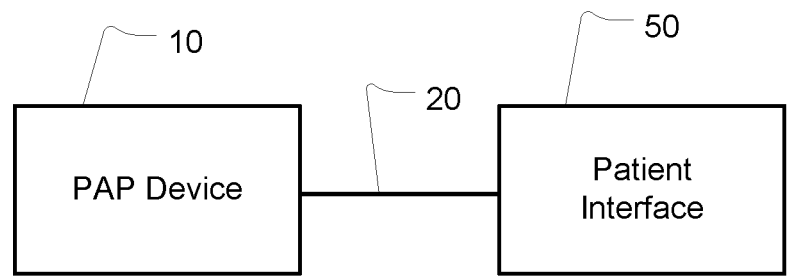
FIG. 1 is a schematic view of an embodiment of a CPAP system.

As schematically shown in FIG. 1, a PAP system (e.g., CPAP system) generally includes a PAP device 10, an air delivery conduit 20 (also referred to as a tube or tubing), and a patient interface 50. In use, the PAP device 10 generates a supply of pressurized air that is delivered to the patient via an air delivery conduit 20 that includes one end coupled to the outlet of the PAP device 10 and an opposite end coupled to the inlet of the patient interface 50. The patient interface comfortably engages the patient's face and provides a seal. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Figure 2:
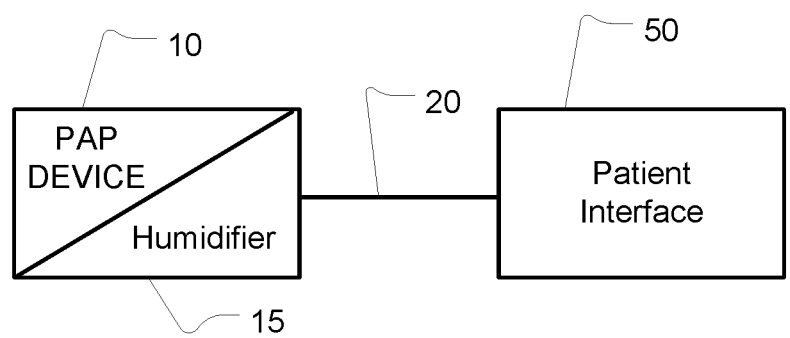
FIG. 2 is a schematic view of another embodiment of a CPAP system.

In embodiments, a humidifier may be incorporated or integrated into the PAP device or otherwise provided downstream of the PAP device. In such embodiments, the air delivery conduit 20 may be provided between the patient interface 50 and the outlet of the humidifier 15 as schematically shown in FIG. 2.

Figure 3:
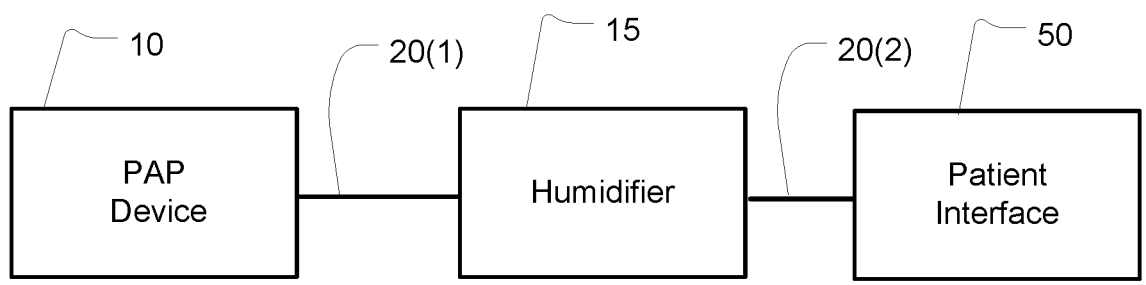
FIG. 3 is a schematic view of another embodiment of a CPAP system.

It should be appreciated that the air delivery conduit may be provided along the air delivery path in other suitable manners. For example, as schematically shown in FIG. 3, the humidifier 15 may be a separate component from the PAP device 10 so that an air delivery conduit 20(1) is placed between the PAP device 10 and the humidifier 15 and another air delivery conduit 20(2) is placed between the humidifier 15 and the patient interface 50.

Generally, a heated humidifier is used to provide sufficient humidity and temperature to the air so that the patient will be comfortable. In such embodiment, the air delivery conduit may be heated to heat the gas and prevent "rain-out" or condensation forming on the inside of the conduit as the gas is supplied to the patient. In this arrangement, the air delivery conduit may include one or more wires or sensors associated with heating.

As described below, each end of the air delivery conduit includes a cuff structured to attach the tube to the patient interface, PAP device, and/or humidifier. The cuffs differ for non-heated tubes and heated tubes, e.g., cuffs for heated tubes accommodate sensors or electronics/wiring associated with heating. The cuffs may include any of those described in U.S. patent application U.S. Ser. No. 12/461,967 incorporated herein in its entirety.

An aspect of the present invention relates to an air delivery conduit between the flow generator and the patient interface with a reduced diameter, e.g., an outer diameter less than the typical 22 mm medical grade tubing (or internal diameter of less than 19 mm). Preferably, the air delivery conduit has an internal diameter of between about 10 mm and about 18 mm, more preferably about 12 mm to 17 mm, or 15 mm. Although other internal diameters may be used such as 11 mm, 12 mm, 13 mm, 14 mm and 16 mm. The reduced diameter will allow the air delivery conduit to be more flexible as the cross-sectional area is reduced and the stiffness of the conduit walls is reduced. The smaller internal diameter conduit may be used to supply pressurized air greater than 15 cmH$_2$0.

Figure 4:
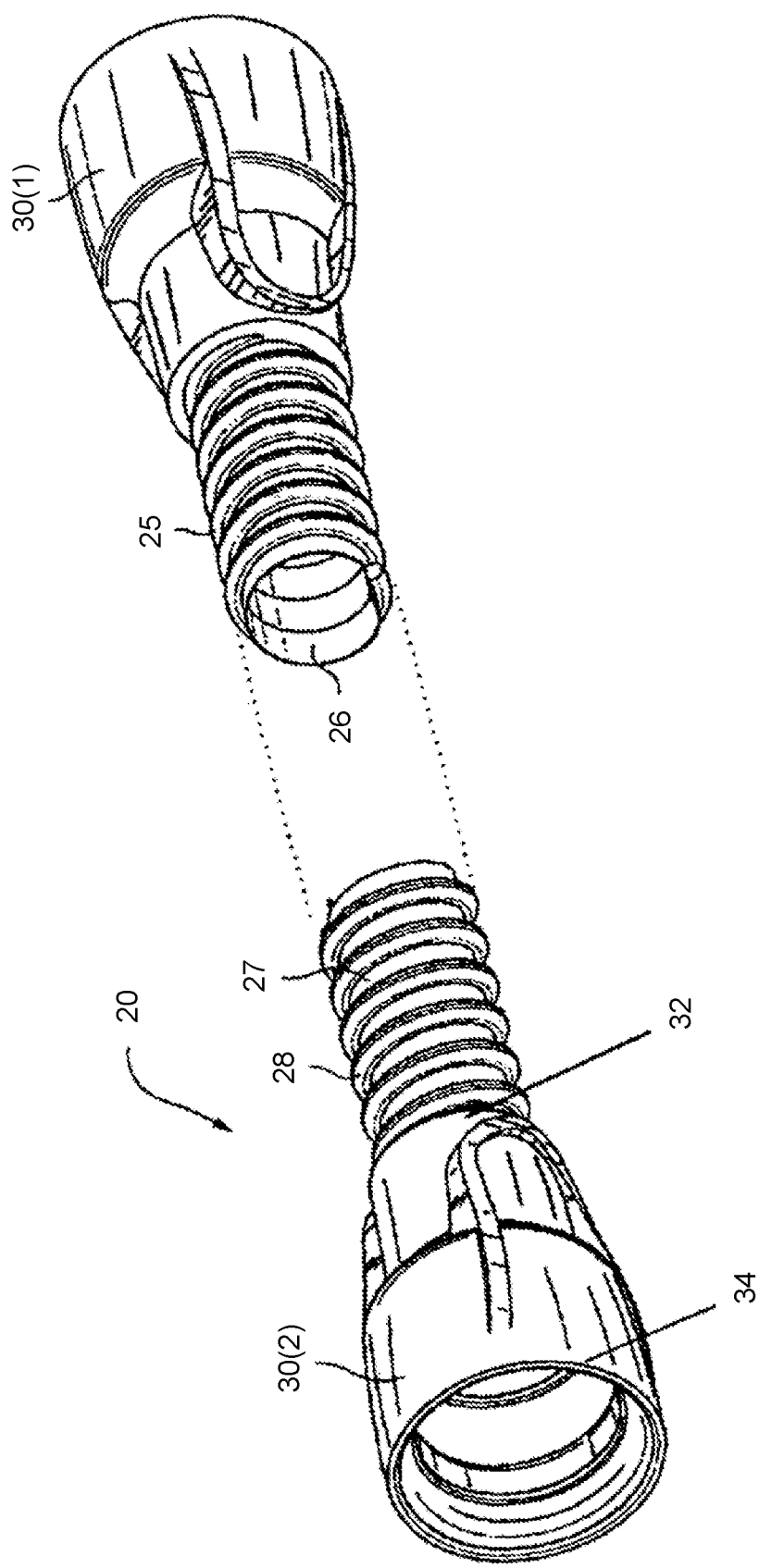
FIG. 4 is a perspective view of an non-heated air delivery conduit including cuffs according to an embodiment of the present invention.

FIG. 4 illustrates an embodiment of an air delivery conduit with non-heated tubing. As illustrated, the air delivery conduit 20 includes a tube 25, a first cuff or connector 30(1) provided to one end of the tube 25 and configured and arranged to engage the outlet of the PAP device or humidifier, and a second cuff 30(2) provided to the opposite end of the tube 25 and configured and arranged to engage the inlet of the patient interface.

In the illustrated embodiment, the tube 25 has a relatively smooth interior surface 26 and an exterior surface 27 provided with flexible spiral ribbing 28. However, the interior and exterior surfaces may provide other suitable configurations, e.g., smooth exterior surface, exterior surface with disc-like annular members, etc. In an alternative embodiment the tube 25 may be made from an integrated textile. In an embodiment, the spiral or helix ribbing 28 has a width of about 0.5 mm to 5 mm, preferably 1-3 mm, e.g., 1 mm, 1.5 mm, 2 mm, or 2.5 mm, a height of about 0.5-2 mm, e.g., 1 mm, 1.5 mm, or 2 mm and a pitch of about 4.5 to 5.5 mm, e.g., 5.2 mm, e.g., to optimize flexibility, minimize noise, and minimize occlusion. The tube 25 has an internal diameter of less than 19 mm, preferably between about 10 mm and 18 mm, more preferably about 12 mm to 17 mm, or 15 mm. In this embodiment, each cuff 30(1), 30(2) is similar to one another.

In another embodiment the tube may not include a spiral or helix ribbing but includes an alternative structural element such as using the 3 electrical wires within the headed tube as a structural support. In such as embodiment the electrical wires may be thicker and made from aluminum or other such electrically conductive elements.

Although only a portion of the tube 25 is shown attached to the cuffs 30(1) and 30(2) it is understood that the tube has a continuous length between the cuffs as indicated by the dotted lines. The tube length may be 1 metre, 1.8 metre, 2 metres, 1980 mm or 1829 mm or any useful length such as smaller length tubes to connect to a nasal mask. Also multiple sections of tubing lengths are also encompassed within the scope of the invention.

As illustrated, the cuff 30 includes a generally cylindrical first end portion 32 and a generally cylindrical second end portion 34. The first end portion 32 is provided (e.g., fixed, co-molded, etc.) to the tube 25 and the second end portion 34 (e.g., with a larger diameter than the first end portion) is removably connectable to a tubular connector provided to the patient interface, PAP device or humidifier.

In an embodiment, the cuff 30 is molded or formed of a resilient rubber-like material, e.g., TPE. The cuff may be coupled or otherwise communicated with the tube 25 in any suitable manner. For example, the cuff may be formed separately from the tube and attached thereto, e.g., friction fit, mechanical interlock, adhesive, etc. Alternatively, the cuff may be integrally formed in one piece with the tube, e.g., molding, co-molding, etc.

Figure 5:
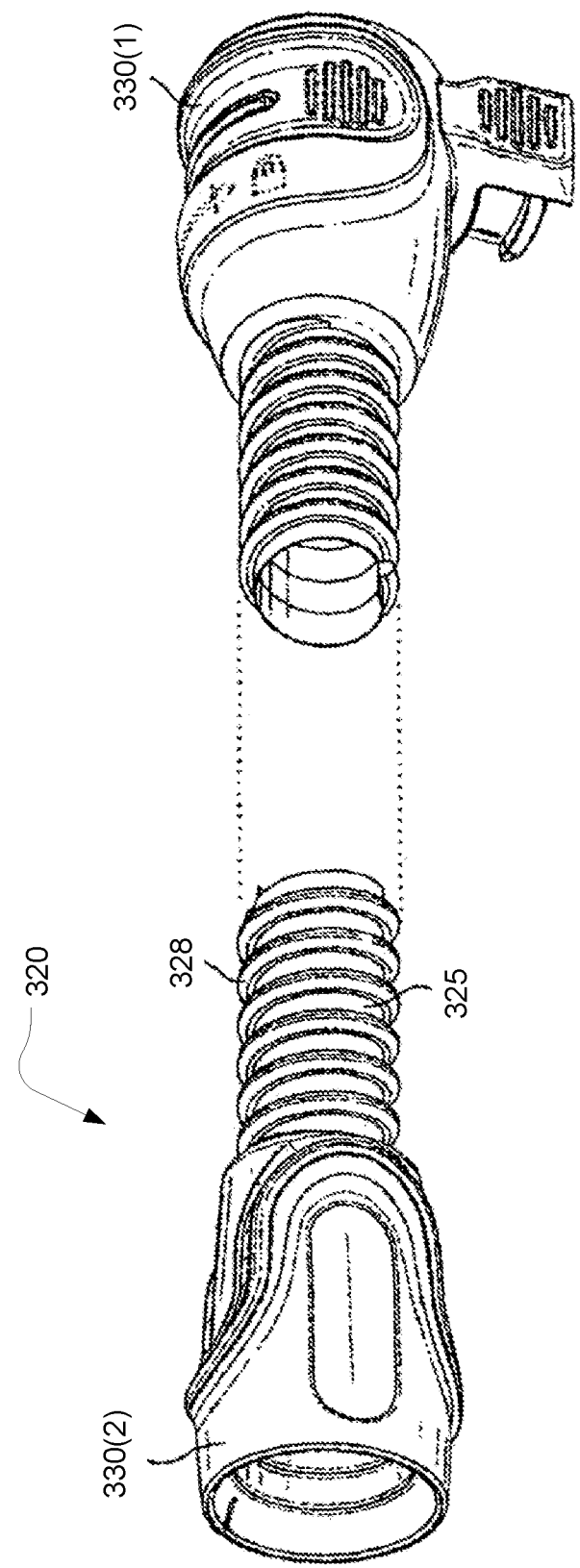
FIG. 5 is a perspective view of a heated air delivery conduit including cuffs according to an embodiment of the present invention.

FIG. 5 illustrates an embodiment of an air delivery conduit with heated tubing. As illustrated, the air delivery conduit 320 includes a tube 325, a first cuff or connector 330(1) provided to one end of the tube 325 and configured and arranged to engage the outlet of the PAP device/humidifier, and a second cuff 330(2) provided to the opposite end of the tube 325 and configured and arranged to engage the inlet of the patient interface.

In this embodiment, the tube 325 is structured to conduct heat along at least a portion of its length. For example, the spiral ribbing 328 of the tube may be structured to support one or more heated wires. In addition, the tube may be structured to support one or more sensing apparatus, e.g., flow sensor, temperature sensor, etc. Further details of such tubing are disclosed in U.S. patent application Ser. No. 11/936,822, filed Nov. 8, 2007, which is incorporated herein by reference in its entirety.

In the illustrated embodiment, the cuffs 330(1), 330(2) are different than one another as described below. However, each cuff provides structure for attaching, sealing, and retaining the cuff to the respective connector, e.g., 22 mm ISO-taper connector. Although only a portion of the tube 325 is shown attached to the cuffs 330(1) and 330(2) it is understood that the tube has a continuous length between the cuffs as indicated by the dotted lines. The tube length may be 1 metre, 1.8 metre, 2 metres, 1980 mm or 1829 mm or any useful length such as smaller length tubes to connect to a nasal mask. Also multiple sections of tubing lengths are also encompassed within the scope of the invention including combinations of heated and non-heated tubing sections.

The air delivery conduit as shown in FIGS. 4 and 5 having a reduced internal diameter provide a smaller surface area than a standard 19 mm internal diameter air delivery conduit. A smaller surface area results in a lower level of heat loss and consequently a reduced risk of rainout within the air delivery tube. Furthermore, a heated conduit having a smaller surface area may require less power to heat the air delivery conduit. The following equations from Fundamentals of Heat and Mass Transfer by Incropera FP & Dewitt DP, 1990, page 99 define a means to determine the heat loss along an air delivery conduit as a function of the diameter of a cylinder along a quanta of conduit. The change in temperature along the conduit is a function of the thermal resistance (R) of the conduit multiplied by the heat transfer (q). The thermal resistance (R) for each element may be calculated using the following equations:

$$R = 1/h_1 2\pi r_1 L$$

$$R = \ln(r_2/r_3)/2\pi k_A L$$

$$R = \ln(r_3/r_2)/2\pi k_B L$$

$$R = \ln(r_4/r_3)/2\pi k_C L$$

$$R = 1/h_4 2\pi r_4 L$$

Wherein $r_1$=internal radius of the conduit film; $r_2$=external radius of the conduit film; $r_3$=external radius of the conduit helix; $r_4=r_3$ or external radius of conduit outer film if used; $k_a$=conduction coefficient of inner film; $k_b$=conduction coefficient (effective) of helix; $k_c$=conduction coefficient of outer film if used; $h_1$=convection coefficient between internal layer and internal air; $h_4$=convection coefficient between external layer and external air; $T_{1-4}$=temperature at various interfaces; L=length of conduit; q=heat transfer rate (w). The heat transfer (q) between layer n and $n+1=(T(n)-T(n+1))*R$, where R=the thermal resistance of each element described in the above equations. The invention is understood to refer to a CPAP system having either a heated or a non-heated air delivery conduit having a reduced internal diameter.

A smaller air delivery conduit is cheaper to manufacture as there is less material required in making the conduit. In use a smaller air delivery conduit may provide improved patient comfort for example if a conduit is bent in use there will be a lower pressure drop due to the bending of the tube. However, a smaller air delivery conduit will cause an increase in impedance within the system. Such an increase in impedance may also lead to increased pressure swings at the patient interface end of the system and may cause discomfort for the patient. The increased impedance needs to be determined and compensated for within the system to allow correct delivery of the desired pressure to the patient.

Pressure at the patient may be controlled by the following algorithm $$P_1 - P_2 = K_1 Q^2 \qquad [\text{eq. 1}]$$

Wherein $P_2$ is the pressure delivered to the patient and $P_1$ is the pressure generated from the blower. Q is flow and $K_1$ is a constant related to the length and diameter of the air delivery conduit. This constant may be determined by length/diameter$^4$ or empirically determined by experiment where it is the co-efficient of the second order term. $K_1 Q^2$ models the turbulent behaviour of the flow, which is the predominant behaviour at such diameter ranges and flow velocities used in such air delivery conduits and therapies. The length and diameter of the air delivery conduit affects the impedance of the system. As the length of the air delivery conduit increases the value of $K_1$ also increases. As the diameter of the air delivery conduit increases the value for $K_1$ decreases. The execution of this algorithm may introduce a delay thus rendering a lag in the motor response resulting in out of phase therapy with the patient breathing. Furthermore, with a reduced tube or conduit diameter, the co-efficient K becomes significant. K is approximately the $4^{th}$ power of the diameter of the tube or conduit. For example, if a 15 mm internal diameter air delivery conduit is connected to the flow generator without adjustment to the correct algorithm, such that the system was operating for a standard 19 mm internal diameter air delivery conduit, the error would be approximately $(19/15)^4$ which may be greater than the clinical requirement for treatment (permissible error of 2 cmH$_2$O) and would fail the Minimum data set (MDS) requirement.

| Mask Type | Hose Length | Constant: K1$^4$ | Constant: K2$^4$ |
|---|---|---|---|
| ResMed Ultra Mirage ™ Nasal mask | 2000 mm 19 mm ID unheated | 1828 | 68 |
| | 1829 mm 15 mm ID unheated | 6130 | −621 |
| | 1980 mm 15 mm ID Heated | 6795 | −602 |
| ResMed Full Face mask | 2000 mm 19 mm ID | 1850 | 750 |
| | 1829 mm 15 mm ID unheated | 6378 | −968 |
| | 1980 mm 15 mm ID Heated | 6142 | 365 |
| ResMed Mirage Swift ™ II Nasal Pillows | 2000 mm 19 mm ID unheated | 3724 | 92 |
| | 1829 mm 15 mm ID unheated | 8070 | −1097 |
| | 1980 mm 15 mm ID Heated | 7820 | −2100 |
| ResMed Nasal Std Mask | 2000 mm 19 mm ID unheated | 2056 | 5 |
| | 1829 mm 15 mm ID unheated | 6779 | −363 |
| | 1980 mm 15 mm ID Heated | 6514 | 1942 |
| ResMed Nasal Pillows (Swift ™ LT) | 2000 mm 19 mm ID unheated | 3509 | 441 |
| | 1829 mm 15 mm ID unheated | 8141 | −1006 |
| | 1980 mm 15 mm ID Heated | 7868 | 339 |

In an alternative preferred embodiment the pressure at the patent may be controlled by the following algorithm $$P_1 - p_2 = K_1 Q^2 + K_2 Q \quad [\text{eq. 2}]$$

Wherein $K_1 Q^2$ models the turbulent behaviour of the flow as for equation 1 above and $K_2 Q$ models the laminar behaviour of the flow.

Figure 6:
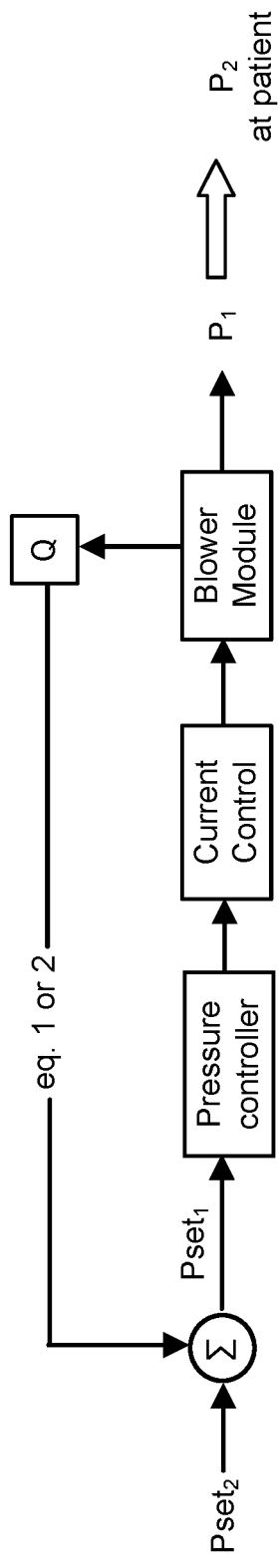
FIG. 6 is a schematic view of a pressure control system for a CPAP system according to an embodiment of the invention.

FIG. 6 is a schematic indicating how the pressure is controlled to compensate for the pressure drop due to the air delivery conduit. Pset2 is the therapy pressure to be delivered that is determined by the therapy selected for delivery by the CPAP system. Pset1 is the pressure set point required to compensate for the pressure drop within the system. Pset1 is calculated from the therapy pressure Pset2+the calculated pressure drop that will occur along the air delivery conduit as determined by equations 1 or 2 above. Pset1 is used to determine the speed of the blower. The pressure generated from the outlet of the blower is indicated as P1. The arrow between P1 and P2 represents the air delivery tube or conduit in which a pressure drop occurs. P2 is the pressure delivered to the patient or patient interface device. In a preferred system P2 is substantially equal to the desired pressure Pset2.

As mentioned above $K_1$ may be determined based on the length of the tube divided by the diameter to the power of 4. Alternatively $K_1$ may be empirically determined by experiment and is the co-efficient of the second order term. $K_2$ is generally measured by experiment by measuring the pressure drop along the system with a range of different components such as AB filters, humidifiers, air delivery conduits and the patient interface devices and combinations thereof attached between the outlet of the blower and the patient interface device. Measurements are taken over a range of different flow levels. The pressure drop may be determined by measuring the pressure difference between the pressure at the blower outlet and the pressure delivered to the patient interface device. The results are then plotted as flow versus pressure drop. Both $K_2$ and $K_1$ may be determined from such plotted results where the fitted curve is then fitted with a second order quadratic equation and the second order term of such an equation is $K_1$ and the first order term is $K_2$. Thus, $K_2$ is calculated to be the linear component of the polynomial or the gradient of the curve. A set of specific $K_1$ and $K_2$ values are determined for each system configuration.

Exemplary co-efficient $K_1$ & $K_2$ of the pressure difference algorithm [eq. 2] above for use with a reduced internal diameter air delivery conduit are within a predetermined range depending on the final diameter of the tube. Examples of the preferred ranges are depicted in the following table:

It is acknowledged that the above values for $K_1$ and $K_2$ are examples only and other values may be used. Generally, when using tubing diameters of between 10-18 mm (or less than 19 mm), the preferred K1 range may be 1850 to 10000; and the preferred K2 range may be −5000 to 3000.

Figure 7:
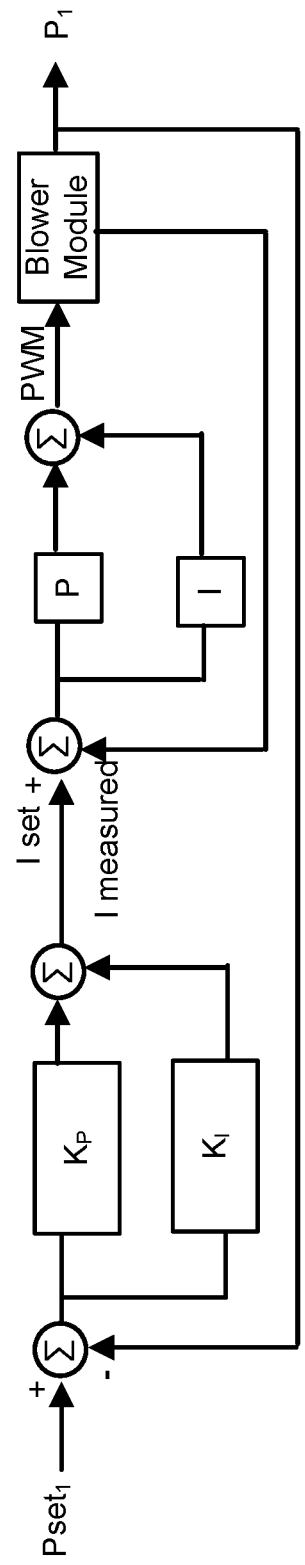
FIG. 7 is a schematic view of pressure controller including a motor PID controller system and PWM system according to another embodiment of the invention.

FIG. 7 shows a schematic of the outer PI (proportional and integral) pressure controller loop and the inner PI current control loop. The pressure controller shown in FIG. 7 is a Proportional Integral Derivative (PID) controller which is designed to correct the set pressure and motor current based on the measured pressure and motor current. The pressure control loop takes the set pressure command Pset and measured output pressure as input to generate a current command for the inner current control loop. The current control loop takes this current command and measured motor current as input to generate a PWM value for motor circuitry. $K_p$ and $K_i$ are the coefficients for proportional and integral parts of the pressure controllers.

The inner PI current control loop in FIG. 7 takes the current command generated from the pressure control loop and the measured motor current as inputs to generate a pulse width modulation (PWM) value for the motor circuitry. The current is measured Imeasure and compared to the set current Iset to maintain the current at the appropriate Iset level. P and I are the coefficients for proportional and integral parts of the current controller.

In an embodiment, the smaller internal diameter conduit is used with a low inertia motor and blowers such as that described in International Patent Applications PCT/AU2006/001617 (published as WO 2007/048206) and PCT/AU2007/000719 (published as WO 2007/134405) and U.S. patent application U.S. Ser. No. 12/155,528 (published as US 2008/0304986), which are incorporated herein in their entirety. Lower inertia motor and blowers provide faster response times and use less power. Such low inertia designs may provide greater pressure rise and fall times. It is to be understood that a low inertia blower is defined as a blower having an inertia less than 5000 g·mm², preferably less than 3000 g·mm² and more preferably less than 2000 g·mm², such as approximately 1500 g·mm² or 1130 g·mm².

In an embodiment, the smaller internal diameter conduit is used with a two-quadrant current control in the motor drive. The two-quadrant current motor drive is preferably located on the CPU. In the prior art the current control range was positive values to 0 current. The two-quadrant current control can control a larger range of current from positive to negative currents. Some controllers can only supply (source) current to power the motor. These are 'single-quadrant' controllers. Other controllers, such as two-quadrant controllers can also sink current which is generated by the motor when it runs faster than the speed set by the controller. There are also four quadrant controller that are similar to a two quadrant controller but can also reverse the motor to give the extra quadrants.

A controller that can sink current, as well as source current, will give regenerative braking. Regenerative braking results when the braking energy is fed back to the motor drive system. This energy may also be used in some applications for charging batteries.

Preferably the CPAP system of the invention uses a two quadrant controller. In such a system a controller supplies a voltage to the motor to drive it, and the motor will then generate a back EMF. A motor's back EMF is proportional to the speed of the motor, and generally cancels out the drive voltage. If the motor goes faster, its back EMF rises and the current (caused by the difference between the controller's output voltage and the motor's back EMF) falls. If the motor rotates fast enough, the motor current falls to zero as the back EMF then equals the controller's output. Consequently when the motor rotates even faster, the current must go negative (feeding back into the controller) as the back EMF is now greater than the controller's output voltage. If the controller can accept this current being fed back into it, then braking starts to occur. The controller has to do something with this current. In one embodiment of the invention the current is dumped as resistive heating. Alternatively in a more efficient design the current is fed back into a battery. The motor can rotate faster either due to external interference or due to sudden changes in the current set point. If the current set point is suddenly reduced due to a new (lower pressure) setting the effective voltage applied across the motor windings drops below back EMF. Hence the current direction reverses. Back EMF becomes the source for the current. Reversal of current direction means reversal of motor magnetic field which tries to turn the motor in the opposite direction which ends up acting as an electrical brake for the motor. However due to its braking action the back EMF source also starts diminishing as the motor slows down. Therefore the amount of braking or control over braking depends on the back EMF rather than an independent voltage source.

In an embodiment, the smaller internal diameter conduit is used with an improved motor current control by the software in the form of a PI loop. For example, the motor current control software has a current control at 50 kHz that may be used which allows for reduced delay in motor response and more precise control In one embodiment the CPAP system includes a low inertia blower, a reduced diameter air delivery conduit and a patient interface device, wherein the calculation of the pressure compensation in the system uses an appropriate Ki coefficient as described in equation 1 above. It is to be understood that a low inertia blower is defined as a blower having an inertia less than 5000 g·mm², preferably less than 3000 g·mm² and more preferably less than 2000 g·mm², for example approximately 1500 g·mm² or 1130 g·mm². Optionally the system may also include the use of a two quadrant current controller, improved current control software such as a PI loop, and/or a high bandwidth flow sensor as described below and/or any combination thereof to compensate for the increased pressure swings and/or impedance resulting from using a reduced internal diameter air delivery conduit.

In a further embodiment the CPAP system includes a low inertia blower, a reduced diameter air delivery conduit and a patient interface device, wherein the calculation of the pressure compensation in the system uses the appropriate $K_1$ and $K_2$ coefficients as described in equation 2 above. Optionally the system may also include the use of a two quadrant current controller, an improved current control software such as a PI loop, and/or a high bandwidth flow sensor as described below and/or any combination thereof to compensate for the increased pressure swings and/or impedance resulting from using a reduced internal diameter air delivery conduit. The two-quadrant controller improves the sudden braking action for example when changing from a high speed to a low speed. The two-quadrant controller can use the current in the reverse direction to allow the motor to stop faster.

As a result of the above features, the air delivery conduit may be smaller, less intrusive, and more acceptable to the patient. In addition, the above features have the capability to increase the compliance of the air delivery conduit among patients.

To use an air delivery conduit with a smaller diameter, e.g., 10 mm to 18 mm internal diameter, or 12 mm to 17 mm internal diameter or 15 mm internal diameter, the pressure output requirements of the flow generator should be capable of responding quickly to provide sufficient pressure outputs. Thus, the performance of the flow generator is very important in providing adequate CPAP therapy. Therefore, the flow generator should know when a smaller diameter air delivery conduit is being used to enable correct performance.

Consequently, one aspect of the present invention relates to a recognition system for the CPAP system that is structured to signal the flow generator the type (e.g., size, length, etc.) of air delivery conduit being attached. This allows the flow generator to recognize or identify the air delivery conduit selected by the patient so that appropriate operating parameters of the flow generator may be selected, e.g., automatically selected, to coordinate with the selected air delivery conduit. Thus, the flow generator can operate more efficiently as the flow generator can select operating parameters that are specifically optimized for the selected air delivery conduit.

In an embodiment, the recognition system includes thermistors within the heated air delivery tube having different resistance valves that are recognized by the air delivery control system within the system as described in U.S. provisional application U.S. 61/230,128 filed 31 Jul. 2009 which is incorporated herein in its entirety. For each tube type used within the system there should not be an overlap in the resistances obtained from using the different thermistors within the specified operating temperature range of the heated tube, for example between 0° C. and 45° C., preferably between −5° C. and 50° C. For example a 15 mm internal diameter heated tube may include a temperature sensor with a thermistor value of 10K and a 17 mm internal diameter heated tube may include a temperature sensor with a thermistor value of 100K. This allows the thermistor resistance value (or sensed voltage) to be used to detect the type of heated tube being used in the system. Thus, any compensation for air path performance can be adjusted automatically (without user intervention) for each tube type, if required.

In one embodiment the system may be adapted to allow automatic recognition of the air delivery conduit attached to the flow generator. The flow generator may then automatically adjust the operating parameters to ensure the best performance of the system for the specific air delivery conduit being used.

In an alternative embodiment the specific type of air delivery conduit selected for use may be manually entered into the device. For example the user, patient or clinician may enter the specific type of air delivery conduit being utilized. As above the system will then adjust the performance to compensate for the specific air delivery conduit.

In a further embodiment of the invention the use of a smaller diameter of air delivery conduit may be compensated for by predicting the pressure disturbances along the conduit and adjusting the pressure output based on these predicted disturbances. Pressure disturbances are pressure swings at the patient interface and can be uncomfortable for the user or patient. Such a system is adapted to pre-empt or predict changes in pressure caused by a variety of disturbances. There are several sources of disturbances within a PAP system, for example changes in patient flow; changes in flow within the flow generator such as in a Bilevel CPAP system changing from IPAP to EPAP pressure levels or in response to expiratory pressure relief; high pressure drops along the conduit due to using reduced conduit diameters; and dynamic conduit diameter changes varying with different pressures and other such disturbances. Such flow disturbances can be compensated for using a hose drop compensation in a feedback control. For any feedback system there is inherently a delay in the system response as the feedback relies upon the system. This is true for a hose drop compensation feedback where there is a delay in the system for the new set pressure to be realized, with the delay increasing as the level of hose drop compensation increases. With feedback control systems the change in pressure has to have happened for it to be detected and then compensated for. Thus, when using a reduced diameter conduit there is an increase in the delay in achieving the desired set pressure as result of an increase in the level of the pressure compensation required due to the higher impedance of the conduit.

It has been found that measured flow can be used as an input to predict disturbances and then make an adjustment to the pressure output based on the predicted level of disturbance. The applicants have termed this control flow feedforward control. A gain factor or feedforward scale factor, $K_f$, is used in a calculation with the change in flow to calculate a feedforward output that is used to adjust the pressure output. The gain factor or feedforward scale factor, $K_f$, is based on a previous characterization of the system to determine the level of pressure disturbance that will occur for each of the components of the system at different levels of flow. The calculated feedforward output may be positive or negative depending on the direction of the change in flow, thus the feedforward output either increases or decreases the set pressure resulting in a faster compensation to reduce the pressure disturbance. The flow feedforward control is a preemptive control method that estimates the flow disturbances and counteracts faster than the feedback control system. Thus by its nature the feedforward control provides faster responses. The feedforward and the feedback systems work in parallel to regulate the set pressure level. Feedforward control is based on disturbance (flow) and hence estimates the effect of disturbance on pressure and changes the pressure based on the estimation. The feedback control system is based on actual pressure measurements and makes further adjustments in the set pressure as required, generally smaller adjustments, after the feedforward pressure adjustments to compensate for any differences in desired pressure requirements. Thus, the feedforward controller monitors the flow disturbances to change the pressure first, and then the set pressure is fine tuned by the feedback controller. The final pressure adjustment is a sum of the feedforward output and the feedback output. Thus, the system uses a combination of the flow feedforward control and a feedback control to minimize pressure disturbances in delivering the set pressure to the patient. Flow feedforward control is a control system adapted to overcome the inherent delay with feedback compensation for reductions in pressure along the conduit and is particularly important for systems that include a smaller diameter conduit and consequently higher impedance, i.e. a conduit internal diameter less than 19 mm, such as 13 mm, 14 mm, 15 mm, 16 mm or 17 mm.

Flow feedforward control is determined by monitoring for changes in the measured flow within the system and estimating a change in output pressure based on the level of change to the measured flow. Flow is measured using a flow sensor that is located in the flow generator. Alternatively the flow sensor may be located within the patient interface or air delivery conduit. The flow sensor is preferably a high bandwidth flow sensor. A flow feedforward system responds earlier than a feedback system to counteract the delay in the system response. The determined level of feed forward compensation is added to the output of the controller rather than being added as an input to the controller in a feedback system. Resulting in the output commands being closer to the set pressure level earlier and thus reducing the potential dead or delay time. Kf may be determined experimentally in a system calibration step at the time of manufacture by adjusting the gain until sufficient reduction in pressure swing is observed.

Figure 8:
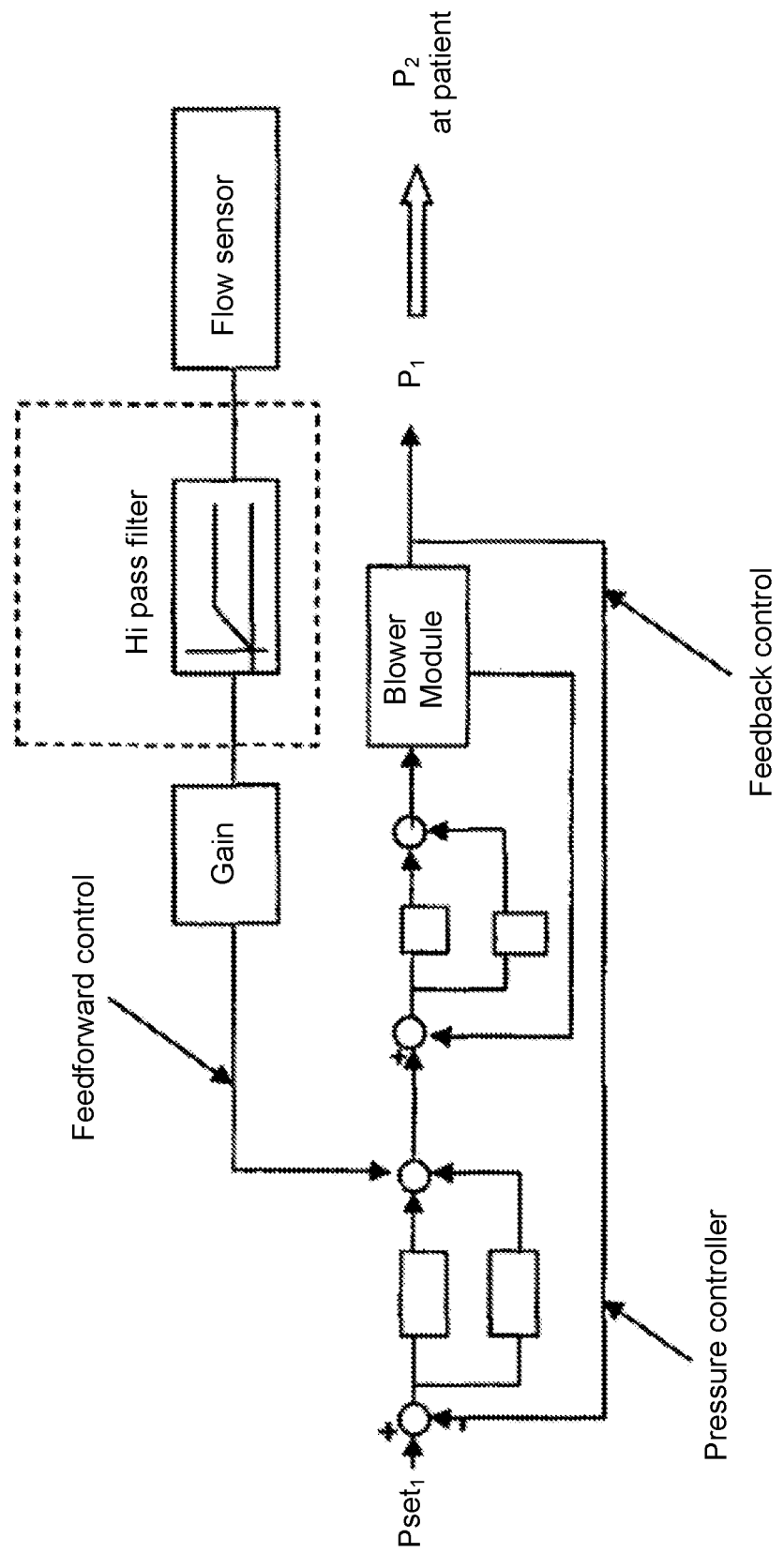
FIG. 8 is a schematic view of flow feedforward system according to an embodiment of the invention.

FIG. 8 shows a schematic of a feed forward control according to an embodiment of the invention. A flow sensor measures the flow and based on disturbances in flow a feedforward output pressure adjustment is calculated by multiplying the change in flow by KF. The determined feedforward output is fed to the PID controller, such as that described in FIG. 7, to compensate for disturbances within the system that are predicted to affect the pressure output P2 to the patient.

In a preferred embodiment, the system also includes a high pass filter, shown in dotted box in FIG. 10. In this embodiment the measured flow signal is filtered through a high pass filter prior to determining the feedforward output. The high pass filter removes the DC component of the measured flow. Alternatively a band pass filter that filters the DC component and high frequencies that are outside the useful range may be used. Alternatively the feedforward output may be based on total flow.

In another embodiment a high resolution flow sensor may be used to improve the accuracy of the feedforward output. In another alternative embodiment the flow may be estimated based on the pressure and motor speed as described in co-pending U.S. application Ser. No. 12/294,957 which is incorporated herein in its entirety.

In another embodiment for a Bilevel PAP device the feedforward control system would be configured to allow the big changes in pressure resulting from switching between EPAP and IPAP pressure, i.e cycling and triggering.

However, the feedforward may compensation for flow disturbances that occur during the IPAP and/or EPAP breathing phase to prevent pressure swings. In this arrangement the controller may provide a signal to the feedforward control when triggering or cycling is occurring to prevent any compensation for the flow disturbances detected during these events as the pressure may be adjusted as required by the controller for the phase change.

For the feedback control system the pressure being delivered is measured or determined. A pressure sensor may be located in the flow generator that measures the pressure of the gas exiting the flow generator and determines the delivered pressure. In an alternative arrangement a pressure sensor may be located in a patient interface to directly measure the delivered pressure or in the air delivery conduit, for example near the patient interface end of the air delivery conduit. The feedback system compares the actual delivered pressure, i.e. measured pressure, and compares this to the set pressure to ensure the system is delivering the required set pressure.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A system comprising:
    a flow generator including an outlet, a blower that supplies breathable gas at pressure to the outlet, a pressure sensor that measures a pressure of the gas supplied from the blower, and a flow sensor that measures a flow of the gas supplied from the blower;
    an air delivery conduit coupled to the outlet of the flow generator; and
    an air delivery control system configured to adjust a speed of the blower, at least in part, by:
        estimating a pressure drop that will occur along the air delivery conduit;
        determining a pressure set point from a predetermined therapy pressure and the estimated pressure drop that will occur along the air delivery conduit;
        correcting a difference between the pressure set point and the pressure measured by the pressure sensor with a pressure controller loop;
        determining a feedforward output from the flow measured by the flow sensor; and
        adjusting an output of the pressure controller loop with the feedforward output.
2. The system of claim 1, wherein the blower supplies the breathable gas at a pressure of 3-25 cmH2O.
3. The system of claim 2, wherein the air delivery conduit includes a conduit portion having an internal diameter of between about 13 mm to about 16 mm.
4. The system of claim 3, wherein the conduit portion has flexible spiral or helix ribbing with a pitch of about 4.5 to 5.5 mm that supports one or more heated wires.
5. The system of claim 3, wherein the conduit portion is made from an integrated textile.
6. The system of claim 1, wherein the air delivery conduit includes one or more heated wires.
7. The system of claim 1, wherein the pressure controller loop is a proportional integral (PI) controller.
8. The system of claim 1, wherein the pressure controller loop is a proportional integral derivative (PID) controller.
9. The system of claim 8, wherein the flow measured by the flow sensor is filtered through a high pass filter prior to determining the feedforward output.
10. The system of claim 1, wherein the feedforward output is further determined from a gain factor that is related to predicted pressure disturbances of one or more components of the system.
11. The system of claim 1 further comprising:
    a patient interface, wherein the flow generator is coupled to a proximal end of the air delivery conduit, and wherein the patient interface is coupled to a distal end of the air delivery conduit.
12. The system of claim 1 further comprising: a recognition system configured to identify a type of the air delivery conduit, wherein the air delivery control system is configured to estimate the pressure drop that will occur along the air delivery conduit based on the type of the air delivery conduit identified by the recognition system.
13. A method comprising:
    supplying, with a blower of a flow generator, breathable gas at pressure to an outlet of the flow generator;
    measuring, with a pressure sensor of the flow generator, a pressure of the breathable gas supplied from the blower;
    measuring, with a flow sensor of the flow generator, a flow of the breathable gas supplied from the blower;
    adjusting, with an air delivery control system, a speed of the blower, at least in part, by:
        estimating a pressure drop that will occur along an air delivery conduit coupled to the outlet of the flow generator;
        determining a pressure set point from a predetermined therapy pressure and the estimated pressure drop that will occur along the air delivery conduit;
        correcting a difference between the pressure set point and the pressure measured by the pressure sensor with a pressure controller loop;
        determining a feedforward output from the flow measured by the flow sensor; and
        adjusting an output of the pressure controller loop with the feedforward output.
14. The method of claim 13, wherein the pressure controller loop is a proportional integral (PI) controller.
15. The method of claim 13, wherein the pressure controller loop is a proportional integral derivative (PID) controller.
16. The method of claim 13, wherein the feedforward output is further determined from a gain factor that is related to predicted pressure disturbances of one or more components of the system.
17. The method of claim 16 further comprising:
    filtering the flow measured by the flow sensor through a high pass filter prior to determining the feedforward output.

18. The method of claim 13 further comprising:
delivering, with the air delivery conduit, the breathable gas supplied from the blower to a patient interface,
wherein the flow generator is coupled to a proximal end of the air delivery conduit, and wherein the patient interface is coupled to a distal end of the air delivery conduit.

19. The method of claim 18 further comprising:
heating, with one or more heated wires of the air delivery conduit, the breathable gas supplied from the blower.

20. The method of claim 13 further comprising:
identifying, with a recognition system, a type of the air delivery conduit,
wherein the pressure drop that will occur along the air delivery conduit is estimated based on the type of the air delivery conduit identified by the recognition system.

* * * * *